United States Patent [19]

Partenheimer et al.

[11] Patent Number: 5,081,290
[45] Date of Patent: Jan. 14, 1992

[54] PROCESS FOR MAKING AROMATIC POLYCARBOXYLIC ACIDS AND OXIDATION CATALYST SYSTEM

[75] Inventors: Walter Partenheimer, Naperville; Diane J. Graziano, Clarendon Hills, both of Ill.

[73] Assignee: Amoco Corporation, Chicago, Ill.

[21] Appl. No.: 541,617

[22] Filed: Jun. 21, 1990

[51] Int. Cl.$^5$ .................. C07C 51/265; B01J 31/00
[52] U.S. Cl. ..................... 562/416; 502/169; 502/170; 502/171; 502/227; 502/228; 502/229; 562/417; 562/480; 562/488
[58] Field of Search .............. 562/416, 417; 502/169, 502/170, 171, 227, 228, 229

[56] References Cited

U.S. PATENT DOCUMENTS 4,716,245 12/1987 Hirose ................................. 562/416
4,876,386 10/1989 Holzhauer et al. ................. 562/414
4,950,786 8/1990 Sanchez et al. ..................... 562/416

Primary Examiner—Jose G. Dees
Assistant Examiner—Vera C. Clarke
Attorney, Agent, or Firm—Gunar J. Blumberg; William H. Magidson; Ralph C. Medhurst

[57] ABSTRACT

There is provided a process for the partial oxidation of a polymethylbenzene to the corresponding aromatic polycarboxylic acid, which process comprises contacting in a reaction zone said polymethylbenzene with molecular oxygen in the presence of an oxidation catalyst comprising at least one heavy-metal compound, said heavy-metal compound being acetate free, a source of bromine, and a non-metal acetate compound, the concentration of acetate in the reaction zone being employed to control the rate of oxidation and the selectivity of oxidation.

There is also provided the catalyst that is employed in the process.

29 Claims, 2 Drawing Sheets

Fig. 1

PROCESS FOR MAKING AROMATIC POLYCARBOXYLIC ACIDS AND OXIDATION CATALYST SYSTEM

BACKGROUND OF THE INVENTION

1. Field of the Invention

This invention relates to the liquid-phase oxidation of an alkyl aromatic with an oxygen-containing gas at an elevated temperature and pressure and in the presence of an oxidation catalyst. More particularly, it relates to an improvement in the process for the oxidation of polymethylbenzenes to aromatic polycarboxylic acids in the presence of a reaction medium comprising a monocarboxylic acid, such as acetic acid, and a catalyst system comprising one or more heavy metals and bromine.

2. Description of the Prior Art

In U.S. Pat. No. 2,833,816, Saffer, et al, disclose a process for producing an aromatic polycarboxylic acid wherein an aromatic compound selected from polyalkyl aromatic compounds and intermediate oxygenated derivatives thereof is oxidized in a liquid phase with molecular oxygen in the presence of a catalyst comprising bromine and a heavy-metal oxidation catalyst. A reaction medium, such as an aliphatic monocarboxylic acid containing about 1 to 8 carbon atoms, is added when needed.

Kamiya reports in "Tetrahedron"; Vol 22, page 2029 (1966), that the induction period in the cobalt (II) dibromide catalyzed oxidation of tetralin could be eliminated by the addition of sodium acetate.

Hay, et al, report in "Autooxidation Reactions Catalyzed by Cobalt Acetate Bromide", page 1306 (1964) that the initial oxidation of cumene was faster with a cobalt (II) dibromide catalyst than with a cobalt (II) acetate/hydrogen bromide mixture.

Sheherbina and Lysukho report in KINETIKA I KATALIZ, 19, page 1076 (1978) that the addition of metal acetates to the oxidation of durene, pseudocumene, and p-xylene in glacial acetic acid by oxygen at a temperature of 95° C. (203° F.) and atmospheric pressure in the presence of a cobalt bromide catalyst almost eliminated completely relatively long induction periods. Acetates of sodium, potassium, barium, zinc, cobalt, or manganese were found to promote this type of oxidation process in the presence of a cobalt bromide catalyst.

Ariko, Samtsevick, and Mitskevich report in a paper to the Institute of Organophysical Chemistry of the Academy of Sciences, Belorussian SSR that the introduction of magnesium acetate to a cobalt bromide catalyst decreased the rate of carbon dioxide formation during the oxidation of p-xylene in the presence of acetic acid.

As shown hereinafter, the oxidation of pseudocumene in the presence of a catalyst consisting of cobalt tetrafluoroborate and manganese dibromide would initiate briefly and then die. Now it has been found that by using a catalyst comprising at least one non-acetate-containing, heavy-metal compound, a source of bromine, and a non-metal acetate compound as the oxidation catalyst, one can control more easily the rate of oxidation and the selectivity of oxidation by means of the acetate concentration that is used.

SUMMARY OF THE INVENTION

According to the present invention, there is provided an improved process for the partial oxidation of a polymethylbenzene to the corresponding aromatic polycarboxylic acid, which process comprises contacting a feed stream comprising the polymethylbenzene with an oxygen-containing gas in the presence of a reaction medium comprising a monocarboxylic acid, such as acetic acid, and an oxidation catalyst comprising at least one acetate-free, heavy-metal compound, a source of bromine, and a non-metal acetate compound. The acetate concentration is used to control the rate of oxidation and the selectivity of oxidation. Preferably, the non-metal acetate compound is used to regulate the acetate concentration.

An embodiment of this process is a process for the partial oxidation of p-xylene to terephthalic acid.

There is provided also the catalyst system that is employed in the process of the present invention.

BRIEF DESCRIPTION OF THE DRAWINGS

The accompanying

DESCRIPTION AND PREFERRED EMBODIMENTS

An important group of commercial processes are those processes for the partial oxidation of an alkyl aromatic with molecular oxygen. Examples of such processes are those wherein a polymethylbenzene is oxidized to its corresponding aromatic polycarboxylic acid, e.g., p-xylene is oxidized to terephthalic acid and pseudocumene (1,2,4-trimethylbenzene) is oxidized to trimellitic acid. Such benzene di- and tricarboxylic acids have wide industrial applications, including the manufacture of polyesters, polyamides, fibers, and films.

Many different polyalkylaromatic compounds are capable of being oxidized to aromatic dicarboxylic acids. Typical examples are shown hereinbelow in Table 1.

TABLE 1

POLYALKYLAROMATICS AND CORRESPONDING AROMATIC ACIDS

| Polyalkylaromatic | Aromatic Carboxylic Acid |
|---|---|
| p-xylene | terephthalic acid |
| m-xylene | isophthalic acid |
| o-xylene | o-phthalic acid |
| 1,2,4-trimethylbenzene (pseudocumene) | trimellitic acid |
| 1,2,4,5-tetramethyl-benzene (durene) | pyromellitic acid |
| 2,6-dimethylnaphthalene | 2,6-naphthalene dicarboxylic acid |
| 2,6-diisopropylnapthalnene | 2,6-naphthalene dicarboxylic acid |

In the case of terephthalic acid, more than ten billion pounds are produced annually throughout the world. Hence, an improved process for manufacturing this benzene polycarboxylic acid, as well as others, will provide a technical advance in the art and will be greeted favorably.

It is well known that numerous aromatic polycarboxylic acids may be prepared conveniently by the catalytic oxidation of alkyl-substituted aryl compounds via molecular oxygen. Such oxidation is effected by reacting the alkyl-substituted aryl compound with molecular oxygen in the conjoint presence of catalytic amounts of a heavy-metal catalyst and of bromine.

Typically, the heavy-metal catalyst comprises a member of the group consisting of manganese, cobalt, nickel, chromium, vanadium, molybdenum, tungsten, tin, cerium, zirconium, titanium, hafnium, and mixtures thereof. These metals, as well as others that have atomic numbers that are not greater than 84, are suitable for this oxidation catalyst and are presented in the "Periodic Chart of the Elements" on pages 58 and 59 of LANGE'S HANDBOOK OF CHEMISTRY, 6th edition, published by Handbook Publishers, Inc, Sandusky, Ohio, 1946. A preferred heavy-metal catalyst comprises manganese and cobalt. The metal of the oxidation catalyst may be added in the elemental, combined, or ionic form. In addition, the bromine of the oxidation catalyst may be added in the elemental, combined, or ionic form. The metal or metals may be supplied in the form of metal salts of a lower aliphatic carboxylic acid, such as a metal acetate, in the form of an organic complex, such as an acetylacetonate, or as metal salts, such as the borates, halides, and nitrates. Bromine may be added as ionic bromine, such as ammonium bromide, hydrobromic acid, or other bromine compound that is soluble in the reaction medium. Potassium bromide, tetrabromoethane, and benzyl bromide are suitable sources of bromine.

When the catalyst comprises soluble forms of cobalt, manganese, and bromine, cobalt (calculated as elemental cobalt) is present in an amount within the range of about 0.5 to about 10 milligram atoms (mga) per gram-mole of the alkyl aromatic; manganese (calculated as elemental manganese) is present in an amount within the range of about 0.1 to about 10 mga per mga of cobalt (calculated as elemental cobalt); and bromine (calculated as the ion) is present in an amount within the range of about 0.2 to about 1.5 mga per mga of total cobalt and manganese (both calculated as the elemental metals).

It has now been found that when oxidizing a polymethylbenzene to an aromatic polycarboxylic acid, the acetate concentration may be used to control the rate of oxidation and the selectivity of oxidation. For example, it has been found that if one starts with a catalyst system comprising acetate-free, heavy-metal compounds and a source of bromine and then adds a non-metal acetate compound to the catalyst system, oxidation will occur and the rate of oxidation and selectivity of oxidation can be controlled.

It is contemplated that at least one acetate-free, heavy-metal compound will be used in the catalyst system of the process of the present invention. This does not exclude the use of a metal acetate or a transition metal acetate. The catalyst system may comprise an acetate-free transition metal compound, as well as an acetate-containing transition metal compound or acetate-containing metal compound. For example, the catalyst system may comprise cobalt acetate and manganese perchlorate. In any event, at least one acetate-free, heavy-metal compound must be present in the catalyst system that is employed in the process of the present invention.

Heavy metals that are suitable for use in the catalyst system of the process of the present invention are the same as those listed hereinabove.

Accordingly, one or more acetate-free, heavy-metal compounds may be used to make the catalyst that is employed in the process of the present invention. Typical examples are metal tetrafluoroborates, such as cobalt tetrafluoroborate, and metal perchlorates, such as manganese perchlorate. Others are cobalt bromide, cobalt carbonate, cobalt chloride, cobalt oxide, cobalt nitrate, cobalt oxalate, cobalt sulfate, cobalt phosphate, cobalt pentanedionate, and compounds of manganese having the same anions.

Another component of the catalyst system of the process of the present invention is a non-metal acetate compound. A typical non-metal acetate compound that is suitable for use in the catalyst system of the present invention is ammonium acetate. Another is tetrabutylammonium acetate.

The oxidation reaction is conducted at a temperature within the range of about 100° C. (212° F.) to about 275° C. (527° F.), desirably within the range of about 130° C. (266° F.) to about 250° C. (482° F.), and preferably within the range of about 170° C. (338° F.) to about 225° C. (437° F.). It is carried out under essentially liquid-phase conditions. The temperature and pressure should be so regulated as to provide a liquid phase in the reaction zone. Generally, the pressure is maintained within the range of atmospheric to about 10,440 kPa (1,500 psig).

The oxidation is carried out with an oxygen-containing gas as a source of molecular oxygen. The gas may be 100% oxygen or a gas mixture containing a lower concentration of oxygen, e.g. air.

The reaction time should be sufficiently long to enable a suitable conversion to result, i.e., about 0.5 to about 25 hours, or more. A reaction time within the range of about 0.5 hour to about 4 hours is preferred.

The oxidation is a liquid-phase reaction. The liquid phase may comprise all or a portion of the organic reactant, or it may comprise a reaction medium in which the organic reactant is soluble or suspended. Such reaction medium may be added to facilitate carrying out the desired reaction or recovering desired product(s). This added reaction medium is suitably a monocarboxylic acid relatively stable or inert to oxidation in the reaction system. Typically, the monocarboxylic acid contains 1 to 8 carbon atoms per molecule. Preferably, the acid contains 2 to 4 carbon atoms, e.g. acetic acid.

Suitably, the reaction medium that is employed in the process of the present invention is acetic acid. It is used in an amount to provide a ratio of about 0.1 to about 10 parts by weight reaction medium per part of aromatic material, desirably a ratio of about 0.5 to about 4, and preferably a ratio of about 1 to about 3.5 parts by weight reaction medium per part of aromatic material.

Various embodiments of the typical processes for the oxidation of polymethylbenzenes to aromatic polycarboxylic acids are presented by Saffer, et al, in U.S. Pat. Nos. 2,833,816; 3,089,906; and 3,089,907; by Park, et al, in U.S. Pat. No. 4,053,506; by Schammel, et al, U.S. Pat. No. 4,845,274; by Schammel, in U.S. Pat. No. 4,764,639; and by Zeitlin, et al, in U.S. Pat. No. 4,777,287.

Figure 1:
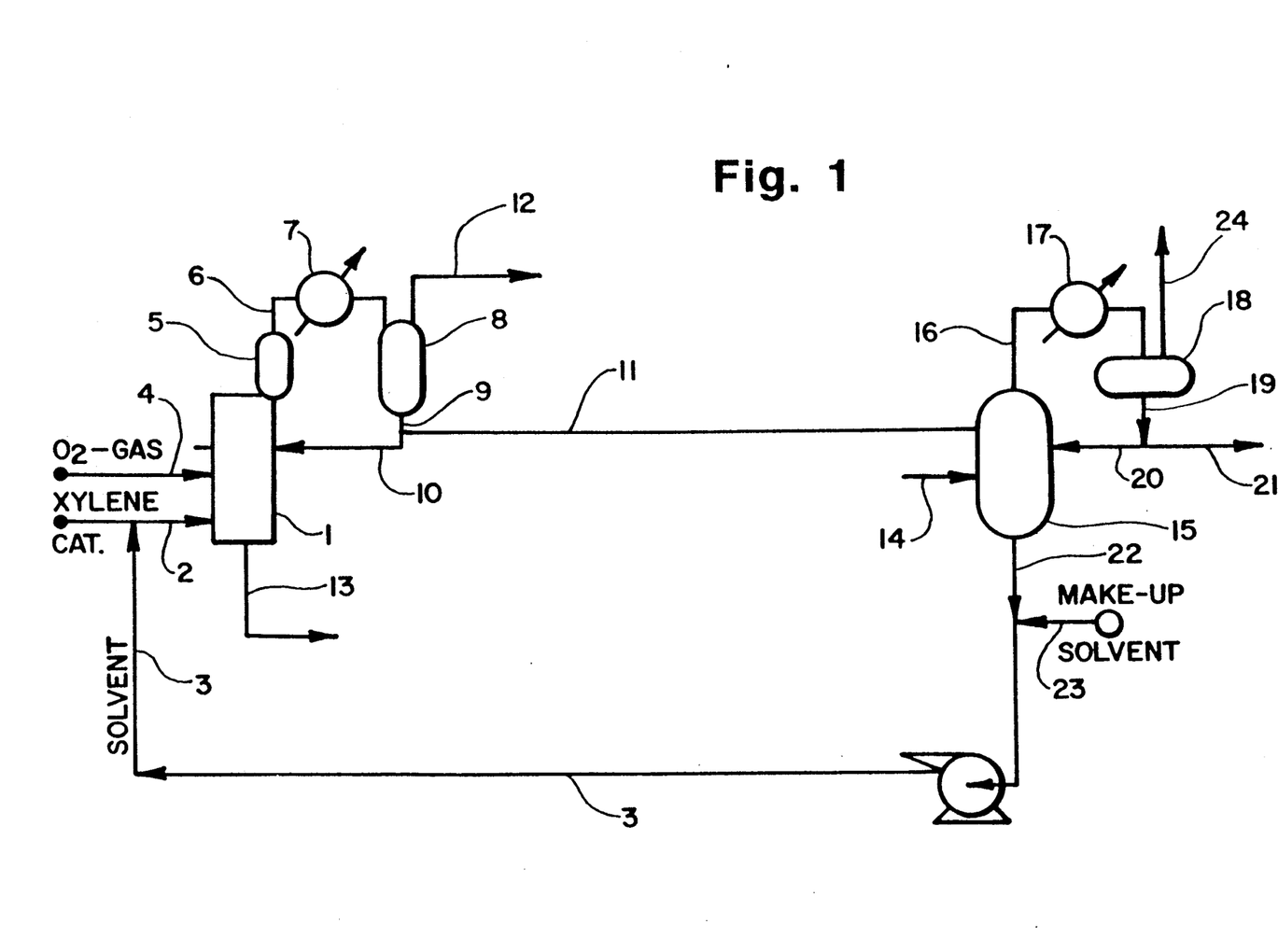
FIG. 1 is a simplified schematic diagram of a typical process for the partial oxidation of p-xylene to terephthalic acid.

Such processes employ a process scheme that is summarized in the accompanying FIG. 1, which provides a simplified process scheme for the partial oxidation of p-xylene to terephthalic acid. This FIGURE does not show various pieces of auxiliary equipment, such as pumps, compressors, and heat exchangers. However, those skilled in the art would recognize the need and location of such equipment.

In this process, the xylene feed and catalyst are introduced into the reaction (oxidation) zone 1 through line 2 after the feed and catalyst have been combined with recycled solvent from line 3. An oxygen-containing gas, such as compressed air, is introduced into reaction zone 1 via line 4. The reaction mixture is stirred or agitated continuously in reaction zone 1, which may exist in the form of one or more reactors or stages. A portion of the reaction zone overhead condensate, which is rich in water, is removed to control effectively the water concentration in the reaction zone 1. Vapors from the reaction zone 1 pass through a primary water-cooled reflux condenser 5. A large portion of the acetic acid solvent contained in the overhead vapor is condensed and removed as liquid reflux to reaction zone 1. Uncondensed vapors pass through line 6 and heat exchanger 7. Additional vapor is condensed, and the condensate is collected in a secondary condenser pot 8. The condensate, which contains water-rich acetic acid, is withdrawn from condenser pot 8 through line 9 to be split into two streams, one of which is returned to reaction zone 1 via line 10 and one of which is passed to solvent recovery through line 11. Any vapor remaining in condenser pot 8 is vented through line 12.

The oxidation-catalyst system employed in this process scheme is one which comprises cobalt and manganese as heavy metals and a source of bromine. The process conditions utilized in this process scheme fall within the ranges of values presented hereinabove.

The terephthalic acid product is removed from reaction zone 1 as fluid oxidation effluent by way of line 13 and is sent to a recovery and purification system (not shown). A suitable recovery and purification system is disclosed in U.S. Pat. No. 4,053,506 by Park, et al.

The condensate in line 11 and solvent vapors obtained from the recovery and purification system in line 14 are charged to distillation column 15 for recovery of acetic acid. Water vapor is removed from column 15 via line 16 through heat exchanger 17. The resulting condensate is collected in condensate drum 18. This condensate is removed from drum 18 through line 19 and is split into two streams, one of which passes through line 20 as reflux to column 15 and one of which is removed in line 21 as discard. Remaining vapor is removed from drum 18 via line 24.

Recovered acetic acid is withdrawn from column 15 through line 22 and is combined with make-up fresh acetic acid from line 23. The resulting acetic acid stream is then passed through line 3 to be combined with the xylene feed and catalyst in line 2, as mentioned hereinabove.

The above-described simplified process scheme will also represent the process of the present invention. However, a different catalyst system is used. In this instance, the catalyst comprises at least one heavy-metal compound, which must be acetate free, a source of bromine, and a non-metal acetate compound, e.g., ammonium acetate.

The catalyst system of the present invention comprises one or more heavy metals and these metals (calculated as elements) are present to provide an amount that is within the range of about 0.1 mga per gm-mole of the polymethylbenzene to about 40 mga per gm-mole of polymethylbenzene feed, preferably within the range of about 0.5 mga per gm-mole of polymethylbenzene to about 10 mga per gm-mole of polymethylbenzene.

If the metals are cobalt and manganese, they will be present in sufficient quantities to provide an amount of cobalt (calculated as elemental cobalt) within the range of about 0.1 mga cobalt per gm-mole of polymethylbenzene to about 40 mga cobalt per gm-mole of polymethylbenzene and an amount of manganese to provide a ratio of manganese to cobalt that is within the range of about 0.1 to about 10. Preferably, these two metals will be present in amounts to provide cobalt in an amount within the range of about 0.1 mga cobalt per gm-mole of polymethylbenzene to about 20 mga cobalt per gm-mole of polymethylbenzene and manganese in an amount that will furnish a ratio of manganese to cobalt that is within the range of about 0.1 to about 5.

Bromine (calculated as the ion) is present in the catalyst system of the present invention in an amount within the range of about 0.1 mga bromine per mga of total heavy metals [calculated as elemental metal(s)] to about 2 mga bromine per mga of total metals, preferably within the range of about 0.2 mga bromine per mga of total heavy metals to about 1 mga bromine per mga of total heavy metals.

Acetate (calculated as the amount added via metal compounds and acetate compounds) will be present in the catalyst system of the present invention in an amount that will provide a ratio of acetate to metals that is within the range of about 0.1 to about 10, preferably within the range of about 0.1 to about 4.

The reaction medium will be used in an amount that will furnish a ratio of medium to polymethylbenzene that is within the range of about 0.1 to about 10, preferably a ratio within the range of about 1 to about 3.5.

The reaction medium may comprise a mixture of the monocarboxylic acid, i.e., acetic acid, and water. The water may be present in an amount that will provide a water concentration that is within the range of about 0 wt % to about 30 wt %, preferably, within the range of about 5 wt % to about 20 wt %.

According to the present invention, there is provided a process for the oxidation of a polymethylbenzene to the corresponding aromatic polycarboxylic acid, which process comprises contacting at elevated temperature and pressure a feed stream comprising said polymethylbenzene in a reaction zone with an oxygen-containing gas in the presence of a monocarboxylic acid reaction medium and an oxidation catalyst while maintaining a liquid phase comprising said medium and said polymethylbenzene in said reaction zone, said catalyst comprising in conjoint presence at least one acetate-free, heavy-metal compound, a source of bromine, and a non-metal acetate compound, the concentration of acetate in said reaction zone being employed to control the rate of oxidation and selectivity of oxidation.

Typically, the reaction medium comprises acetic acid and the non-metal acetate compound is ammonium acetate. Moreover, the amount of the non-metal acetate compound is used generally to vary the concentration of acetate in the reaction zone.

Alternatively or additionally, the acetate concentration may be controlled by the relative amounts of acetate-free, heavy-metal compound and acetate-containing heavy-metal compound when both types of heavy-metal compounds are employed in the catalyst system.

In this improved process, the improvement comprises employing a catalyst comprising at least one heavy-metal compound, said heavy-metal compound being acetate free, a source of bromine, and a non-metal acetate compound and controlling the rate of oxidation and selectivity of oxidation via the concentration of acetate in the reaction zone.

There is provided also the catalyst that is employed in the oxidation process of the present invention.

The following examples are presented to facilitate an understanding of the present invention and to illustrate the present invention and are not intended to limit the scope of the present invention, which scope is limited solely by the appended claims.

EXAMPLE I

The experimental data in this example were obtained in mini-reactors fabricated from glass and operated at atmospheric pressure and at a maximum temperature which corresponded to the boiling point of the medium anhydrous acetic acid, i.e., 118° C. (244° F.). The oxidation temperature was controlled precisely by an oil bath. The vent oxygen was measured continuously by a Beckman oxygen meter, the output of which was monitored continuously with a Scientific Instrument recorder. A constant flow of 50 ml/min into the reactor was maintained. Gas-chromatographic analyses of the vent gases for oxygen, nitrogen, carbon monoxide, and carbon dioxide were made periodically. The oxygen concentration and flow rate of the vent gas were monitored continuously. Increments of water were added periodically into the reactor to measure the rate of oxidation as a function of water concentration.

For each oxidation reaction, 0.574 gm of manganese (II) dibromide tetrahydrate, 0.684 gm of cobalt (II) tetrafluoroborate hexahydrate, 100.0 ml of acetic acid, and 10.0 ml of pseudocumene were used. The reactor was heated to a temperature of 96° C. (205° F.) to 98° C. (208° F.). Acetate ion was added as ammonium acetate, and the amount used is shown in the following tables as the ratio of acetate to metals.

TABLE 2

EFFECT OF ACETATE CONCENTRATION ON OXIDATION WITH 0.4% WATER

| Run No | Acetate/ Metals | $O_2$ Rate, ml/min | Completion % | Vent $CO_2$, % | % $CO_2$/ Rate |
|---|---|---|---|---|---|
| 1 | 0.0 | 0.12 | 2.4 | 0.042 | 0.354 |
| 2 | 0.25 | 8.48 | 9.1 | 0.403 | 0.0481 |
| 3 | 1.0 | 7.16 | 5.9 | 0.13 | 0.0181 |
| 4 | 2.0 | 7.42 | 4.3 | 0.112 | 0.0151 |
| 5 | 3.0 | 7.86 | 5.6 | 0.113 | 0.0144 |
| 6 | 4.0 | 8.11 | 5.7 | 0.125 | 0.0154 |

TABLE 3

EFFECT OF ACETATE CONCENTRATION ON WITH 5% WATER

| Run No | Acetate/ Metals | $O_2$ Rate, ml/min | Completion % | Vent $CO_2$, % | % $CO_2$/ Rate |
|---|---|---|---|---|---|
| 1 | 0.0 | (0.0) | — | — | — |
| 2 | 0.25 | 0.11 | 15 | 0.121 | 1.1 |
| 3 | 1.0 | 7.24 | 13 | 0.213 | 0.0294 |
| 4 | 2.0 | 6.73 | 11 | 0.175 | 0.026 |
| 5 | 3.0 | 6.72 | 11 | 0.168 | 0.025 |
| 6 | 4.0 | 6.98 | 12 | 0.200 | 0.0287 |

TABLE 4

EFFECT OF ACETATE CONCENTRATION ON OXIDATION WITH 13% WATER

| Run No | Acetate/ Metals | $O_2$ Rate, ml/min | Completion % | Vent $CO_2$, % | % $CO_2$/ Rate |
|---|---|---|---|---|---|
| 1 | 0.0 | (0.0) | — | — | — |
| 2 | 0.25 | (0.0) | — | — | — |
| 3 | 1.0 | 0.08 | 18.6 | 0.069 | 0.85 |
| 4 | 2.0 | 3.48 | 17.4 | 0.275 | 0.079 |
| 5 | 3.0 | 2.95 | 15.2 | 0.182 | 0.0617 |
| 6 | 4.0 | 2.73 | 15.8 | 0.179 | 0.0655 |

TABLE 5

EFFECT OF ACETATE CONCENTRATION ON OXIDATION WITH 20% WATER

| Run No | Acetate/ Metals | $O_2$ Rate, ml/min | Completion % | Vent $CO_2$, % | % $CO_2$/ Rate |
|---|---|---|---|---|---|
| 1 | 0.0 | (0.0) | — | — | — |
| 2 | 0.25 | (0.0) | — | — | — |
| 3 | 1.0 | (0.0) | — | — | — |
| 4 | 2.0 | 1.43 | 19.2 | 0.226 | 0.158 |
| 5 | 3.0 | 1.52 | 16.7 | 0.175 | 0.115 |
| 6 | 4.0 | 1.60 | 17 | 0.163 | 0.102 |

TABLE 6

EFFECT OF ACETATE CONCENTRATION ON OXIDATION WITH 26% WATER

| Run No | Acetate/ Metals | $O_2$ Rate, ml/min | Completion % | Vent $CO_2$, % | % $CO_2$/ Rate |
|---|---|---|---|---|---|
| 1 | 0.0 | (0.0) | — | — | — |
| 2 | 0.25 | (0.0) | — | — | — |
| 3 | 1.0 | (0.0) | — | — | — |
| 4 | 2.0 | 0.67 | — | — | — |
| 5 | 3.0 | 0.938 | 17.5 | 0.168 | 0.179 |
| 6 | 4.0 | 1.12 | 18.3 | 0.158 | 0.173 |

In each of the above tables, the selectively of oxidation is given by the absolute value of the vent carbon oxides or by the vent carbon dioxide divided by the rate of oxidation, i.e., the rate of carbon dioxide evolved divided by the rate of oxygen consumed.

The results shown in these tables illustrate that the acetate concentration does affect the rate of oxidation and the vent carbon dioxide. Since it does affect the vent carbon dioxide, it does affect the selectivity of oxidation.

EXAMPLE II

Para-xylene was reacted with air in a two-liter, titanium-clad autoclave to produce terephthalic acid. The autoclave was equipped with means for controlling temperature, pressure, and air flow and a condensor for returning most of the vaporized solvent and feedstock to the reaction zone.

In each case, the catalyst compounds and acetic acid were placed in the reaction zone, and the resulting mixture was heated to a temperature of 194° C. (382° F.) under an atmosphere of nitrogen. Air was pumped into the reactor, and p-xylene was added at a rate of 0.04 mole/min. The vent gases were analyzed every five minutes for oxygen, carbon monoxide, and carbon dioxide. Vent gas bomb samples were taken at 30 min and 65 min during the run and were analyzed for methyl acetate. In Runs Nos 14 and 15, the air rate was adjusted so that the vent oxygen concentration was as close as possible to 3%. The other runs in this example were performed in the same manner. At the termination of each run, the reactor contents were analyzed for terephthalic acid, 4-carboxylbenzaldehyde, p-toluic acid, trimellitic acid, and methyl acetate.

In each case, the ratio of acetate to metals that was employed is that of the catalyst salts before they were combined. It was assumed that those acids and bases that essentially neutralize each other in water also neutralize each other in acetic acid and mixtures of water and acetic acid. Therefore, as an example, phosphoric acid and hydrobromic acid would neutralize cobalt acetate or sodium hydroxide. The cobalt, manganese, and bromine compounds that were used in this study are listed hereinafter in Table 7. The cobalt concentration was fixed at 350 ppm. The manganese-to-cobalt ratio was fixed at 2.7 moles of manganese per mole of cobalt, and the bromine-to-(cobalt+manganese) ratio was fixed at 0.47 mole bromine per mole of cobalt+manganese. The ratio of acetate to metals provides a strong effect on the oxidation reaction. This is shown in Run No 7 and Run No 8. In each of these runs, the acetate-to-metal ratio was 0.0. In the case of Run No 7, the reaction would not even initiate, while in the case of Run No 8, the reaction initiated and died after 45 minutes. The fact that the reactions were different even though their acetate-to-metal ratios were nominally both 0.0 demonstrates the importance of solvolysis reactions of the catalysts compounds with the acetic acid. Slightly different amounts of acetate were produced in the reaction medium.

Figure 2:
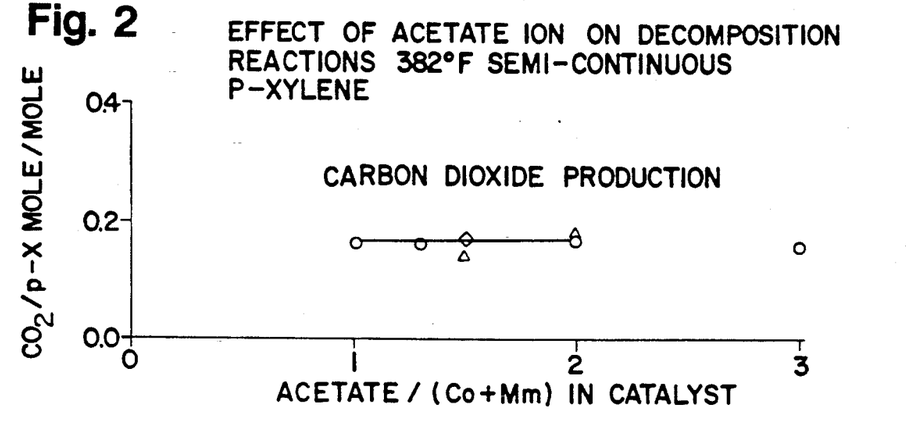
FIGS. 2, 3, and 4 present the effect of acetate ion on the production of carbon dioxide, carbon monoxide, and methyl acetate, respectively, during the oxidation of p-xylene.
Figure 3:
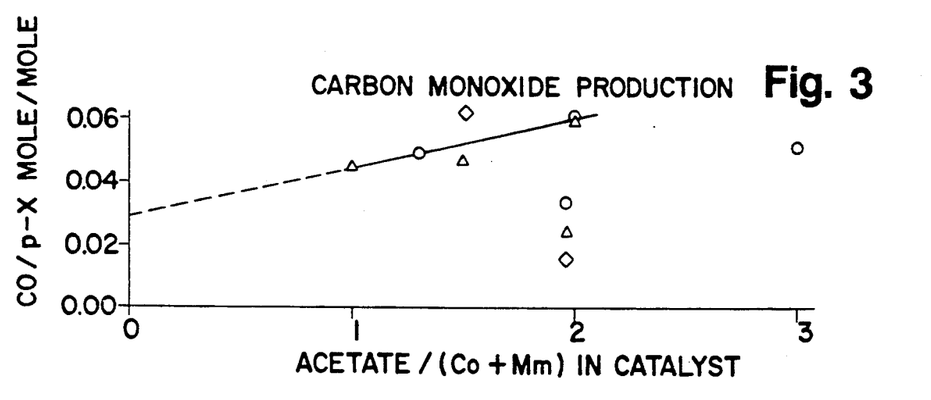
Figure 4:
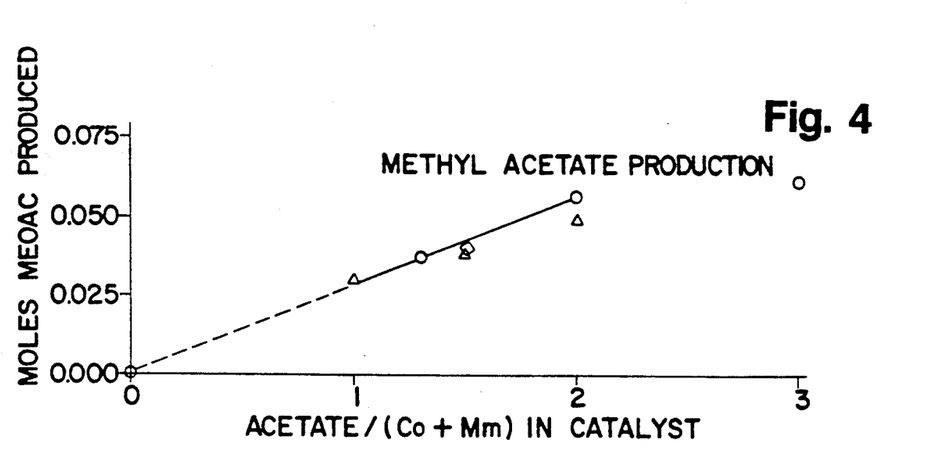

The total amount of oxygen that reacted during each run was determined by numerical integration from the flow rate of air into the reactor and the values obtained in the vent gases. Similarly, the amounts of carbon dioxide and carbon monoxide were determined. The conversion of the p-xylene was defined as the amount of oxygen reacted per the amount of p-xylene in the reaction zone, on a mole-to-mole basis. The rates of carbon dioxide, carbon monoxide, and methyl acetate production as a function of the acetate-to-metals ratio are presented in FIGS. 2, 3, and 4, respectively. Carbon monoxide, carbon dioxide, and methyl acetate were obtained from the decomposition of the p-xylene, intermediates, and acetic acid. Minimum values of their rates of formation are desirable. As shown by FIG. 2, the amount of carbon dioxide that is produced was not significantly affected by acetate-to-metals ratio, while, as shown by FIGS. 3 and 4, the rates of the production of carbon monoxide and methyl acetate were strongly affected by the ratio of acetate to metals.

EXAMPLE III

The runs in this example were conducted in a manner similar to that in Example 1 in order to evaluate the effect of acetate on the oxidation of p-xylene at essentially constant conversion of the feedstock at different water concentrations. Different water concentrations were employed, since water is a product of these oxidations. The tests were performed at 95° C. (203° F.) and at ambient atmospheric pressure. Such testing results in very slow reaction of the p-xylene. Consequently, the rates of formation of carbon dioxide and carbon monoxide and the rate of the reaction at constant conversion of the feedstock were capable of being measured. The rate of oxidation, expressed in terms of ml/min of oxygen reacted, the rate of carbon oxide formation, and the rate of carbon monoxide were evaluated after each water addition. The completion of the reaction was determined by the total amount of oxygen that was reacted at a given point in time. It was assumed that 100% completion occurred when 3 moles of oxygen had reacted per mole of p-xylene. The data are presented hereinafter in Table 8.

The tests were performed as follows: Into a glass reactor, were introduced 0.002 mole of cobalt (II) tetrafluoroborate, 0.002 mole of manganese (II) perchlorate, 0.004 mole of sodium bromide, ammonium acetate (the amounts are presented in Table 8), 20.0 ml p-xylene, and 100.0 ml acetic acid. The resulting solution was heated to a temperature of 95° C. (203° F.) with a stream of air at a rate of 50 ml per minute being passed through the solution via a glass frit. The vent gases were analyzed for oxygen, carbon monoxide, and carbon dioxide. Then an increment of water was added to the reactor, and approximately 45 minutes passed before the vent gases were analyzed again.

The data in FIGS. 2, 3, and 4 were obtained at average values of conversion over the entire oxidation, while Table 8 gives values at a constant p-xylene conversion. For the data in FIGS. 2, 3, and 4, the conversion was varied from 0 to nearly 100%. Optimum rates of oxidation at all water concentrations occurred with a ratio of acetate to metals of about 1. Furthermore, it is shown that the minimum values of carbon monoxide and carbon dioxide production do not always occur at the same ratio of acetate to metals as the maximum rates of oxidation. In addition, minimum values of undesirable decomposition occur with changes in the concen-

TABLE 7

| COMPOUNDS USED AS CATALYST MATEIAL IN EX II[a] | | | | |
|---|---|---|---|---|
| Run No | Acetate/metals, mole/mole | Cobalt Comp'd | Manganese Comp'd | Bromine Source |
| 7 | 0.0 | $ClO_4$—[b] | $ClO_4$— | HBr |
| 8 | 0.0 | $BF_4$—[c] | $BF_4$— | HBr |
| 9 | 1.0 | OAc— + $ClO_4$— | OAc— + $ClO_4$— | HBr |
| 10 | 1.0 | OAC— + $BF_4$— | OAC— + $BF_4$— | HBr |
| 11 | 1.3 | OAc— + fluoride | OAc— + fluoride | HBr |
| 12 | 1.5 | OAc—[d] | OAc— + bromide | $MnBr_2$ |
| 13[e] | 1.5 | OAc— | OAc— | HBr |
| 14 | 2.0 | OAc— | OAc— | HBr |
| 15 | 2.0 | OAc— | OAc— | HBr |
| 16[f] | 3.0 | OAc— | OAc— | HBr |

[a]Metal salts added in their II valence state
[b]Perchlorate anion
[c]Tetrafluoroborate anion
[d]Acetate anion
[e]Phosphoric acid added to control acetate conc. (assumed that one mole of phosphoric acid would neutralize one acetate anion)
[f]Sodium hydroxide added (assumed that one mole of sodium hydroxide reacted with acetic acid to produce one mole of sodium acetate)

tration of the water. As a result, we can change the acetate-to-metals ratios at different points during the reaction depending on the concentration of water and depending on the extent of oxidation.

bromic acid. It was assumed that hydrobromic acid was a strong acid in acetic acid and that one hydrogen bromide neutralized one acetate anion in solution.

The results of these latter runs demonstrate that for

TABLE 8

TESTS CONDUCTED AT CONSTANT CONVERSIONS

| | Run | | | | |
|---|---|---|---|---|---|
| | 17 | 18 | 19 | 20 | 21 |
| $NH_4OAc$, mole | 0.0 | 0.040 | 0.080 | 0.120 | 0.16 |
| OAc/metals, mole/mole | 0.0 | 1.0 | 2.0 | 3.0 | 4.0 |
| Oxid'n rate[a], 5% $H_2O$ | 7.80 | 8.66 | 6.41 | 6.79 | 5.96 |
| Oxid'n rate, 10% $H_2O$ | 4.51 | 6.68 | 4.34 | 3.60 | 2.76 |
| Oxid'n rate, 13% $H_2O$ | 0.60 | 4.35 | 2.50 | 2.20 | 1.75 |
| Oxid'n rate, 17% $H_2O$ | — | 2.67 | 1.69 | 1.53 | 1.26 |
| $CO_2$/rate[b], 5% $H_2O$ | 0.052 | 0.022 | 0.019 | 0.017 | 0.019 |
| $CO_2$/rate, 10% $H_2O$ | 0.114 | 0.046 | 0.028 | 0.028 | 0.033 |
| $CO_2$/rate, 13% $H_2O$ | 0.332 | 0.067 | 0.041 | 0.046 | 0.049 |
| $CO_2$/rate, 17% $H_2O$ | — | 0.107 | 0.064 | 0.061 | 0.065 |
| CO/rate[c], 5% $H_2O$ | 0.012 | 0.0046 | 0.0025 | 0.0018 | 0.0045 |
| CO/rate, 10% $H_2O$ | 0.017 | 0.0086 | 0.0030 | 0.0036 | 0.0034 |
| CO/rate, 13% $H_2O$ | 0.025 | 0.0098 | 0.0101 | 0.0041 | 0.0037 |
| CO/rate, 17% $H_2O$ | — | 0.0144 | 0.0069 | 0.0037 | 0.051 |
| Compl[d] %, 5% $H_2O$ | 7.0 | 8.3 | 7.8 | 9.9 | 9.4 |
| Compl %, 10% $H_2O$ | 10.6 | 12.7 | 10.5 | 11.9 | 11.1 |
| Compl %, 13% $H_2O$ | 11.9 | 14.7 | 11.6 | 13.2 | 11.8 |
| Compl %, 17% $H_2O$ | — | 16.1 | 12.1 | 13.8 | 12.3 |

[a] Values are in ml $O_2$ reacted per minute.
[b] The selectivity to $CO_2$ of the reaction. This is the rate of $CO_2$ formed divided by the rate of $O_2$ consumed.
[c] The selectivity to CO. This is the rate of CO formed divided by the rate of $O_2$ consumed.
[d] Determined from moles of $O_2$ reacted & moles of p-xylene placed in the reactor. Assumed that 3 moles of $O_2$ reacts with 1 mole of p-xylene. compl = completion.

EXAMPLE IV

It is well known that various combinations of metals may be combined with bromine to provide efficient oxidation catalysts. Metals, such as cobalt, manganese, nickel, titanium, zirconium, cerium, copper, and hafnium, whether individually or in various combinations with bromine, are efficient catalysts.

In this example, the effect of the ratio of acetate to metals upon different catalyst combinations was determined. The results of these tests are presented hereinbelow in Table 9. The data for this table were obtained in the same way as the data in Table 8. In these runs, cobalt (II) and manganese (II) acetate salts were used, and the ratio of acetate to metals was varied by replacing sodium bromide as a bromine source by hydrobromic acid. It was assumed that hydrobromic acid was a strong acid in acetic acid and that one hydrogen bromide neutralized one acetate anion in solution.

The results of these latter runs demonstrate that for some catalysts an acetate-to-metals ratio of 2 provides a higher rate of oxidation than a ratio of 1, while for others it does not. Higher rates of oxidation are desirable, since lower catalyst concentrations can be used in the process. This constitutes economic savings. Higher rates are also desirable, since less catalyst components will end up in the product carboxylic acid cakes. As a result, less purification of the cakes is required to remove such contaminates. As shown hereinabove in Table 8, the desirable minimum values of carbon dioxide and carbon monoxide formation often do not occur at the maximum rate of oxidation. However, as shown hereinabove, both the formation of carbon oxides and the rate of oxidation are capable of being controlled by the ratio of acetate to metals.

TABLE 9

EFFECT OF CHANGING THE ACETAE-TO-METALS RATIOS ON OXIDATION OF P-XYLENE

| | Run | | | | | |
|---|---|---|---|---|---|---|
| | 22 | 23 | 24 | 25 | 26 | 27 |
| Catalyst type | Co/Mn/Br | Co/Mn/Br | Co/Br | Co/Br | Mn/Br | Mn/Br |
| Catalyst, mmole[a] | 2/2/4 | 2/2/4 | 4/4 | 4/4 | 4/4 | 4/4 |
| OAc/metals, mole/mole | 2.0 | 1.0 | 2.0 | 1.0 | 2.0 | 1.0 |
| Oxid'n rate, 0.3% $H_2O$ | 5.40 | 5.24 | 5.76 | 5.3 | 1.34 | 1.03 |
| Oxid'n rate, 5% $H_2O$ | 4.46 | 4.10 | 4.61 | 4.72 | 0.61 | 0.96 |
| Oxid'n rate, 10% $H_2O$ | 4.09 | 3.62 | 4.68 | 3.77 | 0.57 | 1.23 |
| Oxid'n rate, 13% $H_2O$ | 2.26 | 3.91 | 4.03 | 3.62 | 0.46 | 1.11 |
| $CO_2$/rate[b], 0.3% $H_2O$ | 0.0158 | 0.0154 | 0.0229 | 0.0205 | 0.140 | — |
| $CO_2$/rate, 5% $H_2O$ | 0.0184 | 0.0166 | 0.0251 | 0.0195 | 0.155 | — |
| $CO_2$/rate, 10% $H_2O$ | 0.0212 | 0.0202 | 0.0259 | 0.0193 | 0.199 | — |
| $CO_2$/rate, 13% $H_2O$ | 0.0343 | 0.0378 | 0.0365 | 0.0335 | — | — |
| CO/rate[c], 0.3% $H_2O$ | 0.0014 | — | 0.0021 | 0.0228 | — | — |
| CO/rate, 5% $H_2O$ | 0.0017 | 0.0022 | 0.0037 | 0.0038 | — | — |
| CO/rate, 10% $H_2O$ | 0.0026 | 0.0028 | 0.0039 | 0.0045 | — | — |
| CO/rate, 13% $H_2O$ | — | 0.0051 | 0.0056 | 0.0056 | — | — |
| Compl[d] %, 0.3% $H_2O$ | 5.40 | 3.10 | 2.70 | — | 5.2 | 4.80 |
| Compl %, 5% $H_2O$ | 4.46 | 6.80 | 6.10 | 3.00 | 5.8 | 5.60 |
| Compl %, 10% $H_2O$ | 8.60 | 8.80 | 9.50 | 8.80 | 6.20 | 6.20 |

TABLE 9-continued

EFFECT OF CHANGING THE ACETAE-TO-METALS RATIOS ON OXIDATION OF P-XYLENE

| | Run | | | | | |
|---|---|---|---|---|---|---|
| | 22 | 23 | 24 | 25 | 26 | 27 |
| Compl %, 13% H$_2$O | 10.2 | 10.2 | 12.0 | 10.9 | 6.5 | 7.00 |

$^a$mmole = millimole
$^b$Selectivity to CO$_2$. This is the rate of CO$_2$ formed divided by the rate of O$_2$ consumed.
$^c$Selectivity to CO. This is the rate of CO formed divided by rate of O$_2$ consumed.
$^d$compl = completion The above examples demonstrate that the acetate-to-metals ratio will strongly effect the oxidation of polyalkylaromatic compounds in the presence of heavy metals-bromine catalysts.

What is claimed is:

1. A process for the oxidation of a polymethylbenzene to the corresponding aromatic polycarboxylic acid, which process comprises contacting at temperature and pressure a feed stream comprising said polymethylbenzene in a reaction zone with an oxygen-containing gas in the presence of a monocarboxylic-acid reaction medium and an oxidation catalyst while maintaining a liquid phase comprising said medium and said polymethylbenzene in said reaction zone, said catalyst comprising in conjoint presence at least one acetate-free, heavy-metal compound, a source of bromine, and a non-metal acetate compound, the concentration of acetate in said reaction zone being employed to control the rate of oxidation and the selectivity of oxidation wherein said temperature is within the range of about 100° C. to about 275° C. and said pressure is within the range of about atmospheric pressure to about 10,440 kPa, and wherein the ratio of acetate to metals is maintained within the range of about 0.1 mga of acetate per mga of metals to about 10 mga of acetate per mga of metals.

2. The process of claim 1, wherein said non-metal acetate compound is ammonium acetate and said medium comprises acetic acid.

3. The process of claim 1, wherein the heavy metal of said heavy-metal compound comprises a metal selected from the group consisting of manganese, cobalt, nickel, chromium, vanadium, molybdenum, tungsten, tin, zirconium, titanium, hafnium, and cerium and the amount of said non-metal acetate compound is employed to vary said concentration of acetate.

4. The process of claim 1, wherein said source of bromine is hydrobromic acid.

5. The process of claim 3, wherein said catalyst comprises a cobalt compound and a manganese compound.

6. The process of claim 3, wherein said non-metal acetate compound is ammonium acetate and said medium comprises acetic acid.

7. The process of claim 5, wherein said non-metal acetate compound is ammonium acetate and said medium comprises acetic acid.

8. The process of claim 6, wherein the ratio of acetate to metals is maintained within the range of about 0.1 mga of acetate per mga of metals to about 10 mga of acetate per mga of metals.

9. The process of claim 2, wherein the ratio of acetate to metals is maintained within the range of about 0.1 mga of acetate per mga of metals to about 10 mga of acetate per mga of metals.

10. The process of claim 7, wherein the ratio of acetate to metals is maintained within the range of about 0.1 mga of acetate per mga of metals to about 10 mga of acetate per mga of metals.

11. The process of claim 10, wherein said catalyst contains sufficient cobalt compound to provide an amount of cobalt within the range of about 0.1 mga of cobalt per gm-mole of polymethylbenzene to about 40 mga of cobalt per gm-mole of polymethylbenzene, sufficient manganese compound to provide a ratio of manganese to cobalt that is within the range of about 0.1 to about 10, and sufficient bromine to provide an amount that is within the range of about 0.1 mga of bromine per mga of cobalt and manganese to about 2 mga of bromine per mga of cobalt and manganese.

12. The process of claim 10 wherein said polymethylbenzene comprises p-xylene and said catalyst contains sufficient cobalt compound to provide an amount of cobalt within the range of about 0.1 mga of cobalt per gm-mole of polymethylbenzene to about 40 mga of cobalt per gm-mole of polymethylbenzene, sufficient manganese compound to provide a ratio of manganese to cobalt that is within the range of about 0.1 to about 10, and sufficient bromine to provide an amount that is within the range of about 0.1 mga of bromine per mga of cobalt and manganese to about 2 mga of bromine per mga of cobalt and manganese.

13. In an improved process for the oxidation of a polymethylbenzene to the corresponding polycarboxylic acid wherein a feed stream comprising said polymethylbenzene is contacted at temperature and pressure in a reaction zone with an oxygen-containing gas in the presence of a reaction medium comprising a monocarboxylic acid and an oxidation catalyst comprising in conjoint presence a heavy-metal catalyst and a source of bromine to produce said polycarboxylic acid, the improvement which comprises employing a catalyst comprising at least one acetate-free, heavy-metal compound, a source of bromine, and a non-metal acetate compound and controlling the rate of oxidation and selectivity of oxidation via the concentration of acetate in the reaction zone wherein said temperature is within the range of about 100° C. to about 275° C. and said pressure is within the range of about atmospheric pressure to about 10,440 kPa, and wherein the ratio of acetate to metals is maintained within the range of about 0.1 mga of acetate per mga of metals to about 10 mga of acetate per mga of metals.

14. The improved process of claim 13, wherein the heavy metal of said heavy-metal compound of said catalyst comprises a metal selected from the group consisting of manganese, cobalt, nickel, chromium, vanadium, molybdenum, tungsten, tin, zirconium, titanium, hafnium, and cerium and the amount of said non-metal acetate compound is employed to vary said concentration of acetate.

15. The improved process of claim 13, wherein said non-metal acetate compound of said catalyst is ammonium acetate.

16. The improved process of claim 13, wherein said source of bromine is hydrobromic acid.

17. The improved process of claim 14, wherein said catalyst comprises a manganese compound and a cobalt compound.

18. The improved process of claim 14, wherein said non-metal acetate compound is ammonium acetate.

19. The improved process of claim 17, wherein said non-metal acetate compound is ammonium acetate.

20. The improved process of claim 18, wherein the ratio of acetate to metals of said catalyst is maintained within the range of about 0.1 mga of acetate per mga of metals to about 10 mga of acetate per mga of metals.

21. The improved process of claim 19, wherein the ratio of acetate to metals of said catalyst is maintained within the range about 0.1 mga of acetate per mga of metals to about 10 mga of acetate per mga of metals.

22. The improved process of claim 21, wherein said catalyst contains sufficient cobalt compound to provide an amount of cobalt within the range of about 0.1 mga of cobalt per gm-mole of polymethylbenzene to about 40 mga of cobalt per gm-mole of polymethlybenzene, sufficient manganese compound to provide a ratio of manganese to cobalt that is within the range of about 0.1 to about 10, and sufficient bromine to provide an amount that is within the range of about 0.1 mga of bromine per mga of cobalt and manganese to about 2 mga of bromine per mga of cobalt and manganese.

23. A catalyst for the partial oxidation of polymethylbenzenes to aromatic polycarboxylic acids, which catalyst comprises at least one heavy-metal compound, said heavy-metal compound being acetate free, a source of bromine, and a non-metal acetate compound wherein the ratio of acetate to metals is maintained within the range of about 01. mga of acetate per mga of metals to about 10 mga of acetate per mga of metals.

24. The catalyst of claim 23, wherein the heavy metal of said heavy-metal compound comprises a metal selected from the group consisting of manganese, cobalt, nickel, chromium, vanadium, molybdenum, tungsten, tin, zirconium, titanium, hafnium, and cerium.

25. The catalyst of claim 23, wherein said non-metal acetate compound is ammonium acetate.

26. The catalyst of claim 24, which catalyst comprises a manganese compound and a cobalt compound.

27. The catalyst of claim 26, wherein said non-metal acetate compound is ammonium acetate.

28. The catalyst of claim 27, wherein the ratio of acetate to metals is maintained within the range of about 0.1 mga of acetate per mga of metals to about 10 mga of acetate per mga of metals.

29. The catalyst of claim 28, wherein said catalyst contains sufficient cobalt compound to provide an amount of cobalt within the range of about 0.1 mga of cobalt per gm-mole of polymethylbenzene to about 40 mga of cobalt per gm-mole of the polymethylbenzene, sufficient manganese compound to provide a ratio of manganese to cobalt that is within the range of about 0.1 to about 10, and sufficient bromine to provide an amount of bromine that is within the range of about 0.1 mga of bromine per mga of cobalt and manganese to about 2 mga of bromine per mga of cobalt and manganese.

* * * * *

UNITED STATES PATENT OFFICE
CERTIFICATE OF CORRECTION

Patent No. 5,081,290         Dated    Jan. 14, 1992

Inventor(s)  Walter Partenheimer and Diane J. Graziano

It is certified that error appears in the above-identified patent and that said Letters Patent is hereby corrected as shown below:

| Col. | Line | |
|---|---|---|
| 12 | 54 | "5.40 5.24 5.76 5.3 1.34 1.03" should read --5.40 5.24 5.76 5.35 1.34 1.03-- |

Signed and Sealed this

Twentieth Day of April, 1993

Attest:

MICHAEL K. KIRK

Attesting Officer            Acting Commissioner of Patents and Trademarks